(12) United States Patent
Cho et al.

(10) Patent No.: US 8,134,278 B2
(45) Date of Patent: Mar. 13, 2012

(54) SURFACE ACOUSTIC WAVE DEVICE AND SURFACE ACOUSTIC WAVE BIOSENSOR

(75) Inventors: Eun Chol Cho, Seoul (KR); Hun Joo Lee, Hwaseong-si (KR); Soo Suk Lee, Suwon-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 59 days.

(21) Appl. No.: 12/700,307

(22) Filed: Feb. 4, 2010

(65) Prior Publication Data
US 2011/0073474 A1 Mar. 31, 2011

(30) Foreign Application Priority Data

Sep. 25, 2009 (KR) .................. 10-2009-0091060

(51) Int. Cl.
*H01L 41/08* (2006.01)
(52) U.S. Cl. ................... 310/313 D; 310/313 R
(58) Field of Classification Search ............. 310/313 A, 310/313 D, 313 R; 333/193–195
See application file for complete search history.

(56) References Cited

U.S. PATENT DOCUMENTS

| 4,472,652 | A | * | 9/1984 | Brice et al. ............. 310/313 B |
| 5,061,870 | A | * | 10/1991 | Ieki et al. ................ 310/313 A |
| 5,283,037 | A | * | 2/1994 | Baer et al. ................ 422/82.01 |
| 6,165,335 | A | * | 12/2000 | Lennox et al. ........... 204/403.01 |
| 6,478,939 | B1 | * | 11/2002 | Lennox et al. ........... 204/403.08 |
| 7,459,991 | B2 | * | 12/2008 | Ruile et al. ................... 333/133 |
| 2007/0000327 | A1 | | 1/2007 | Sung et al. |
| 2007/0284966 | A1 | | 12/2007 | Kadota et al. |

FOREIGN PATENT DOCUMENTS

| JP | 1991-03019031 A | 1/1991 |
| JP | 1996-08181563 A | 7/1996 |
| JP | 2000-12261283 A | 9/2000 |
| JP | 2006-18313092 A | 11/2006 |

* cited by examiner

*Primary Examiner* — Mark Budd
(74) *Attorney, Agent, or Firm* — Leydig, Voit & Mayer, Ltd.

(57) ABSTRACT

A surface acoustic wave device, including: a piezoelectric substrate; an interdigitated transducer electrode disposed on the substrate; an oxide film disposed on surface of the interdigitated transducer electrode; and a hydrophobic film disposed on a surface of the oxide film.

14 Claims, 8 Drawing Sheets

SURFACE ACOUSTIC WAVE DEVICE AND SURFACE ACOUSTIC WAVE BIOSENSOR

CROSS-REFERENCE TO RELATED APPLICATION

This application claims priority to Korean Patent Application No. 10-2009-0091060, filed on Sep. 25, 2009, and all the benefits accruing therefrom under 35 U.S.C. §119, the content of which in its entirety is herein incorporated by reference.

BACKGROUND

1. Field

This disclosure relates to a surface acoustic wave device and a surface acoustic wave biosensor.

2. Description of the Related Art

A surface acoustic wave ("SAW") is not an electromagnetic wave but a mechanical wave that is generated from the movement of particles by external factors, such as thermal, mechanical, and electrical forces, and is propagated by vibrational energy, most of which is concentrated on the surface of a medium. A SAW sensor is a device that senses, e.g., detects, a target material, such as an analyte, using a surface acoustic wave.

Generally, the SAW sensor is disposed on a substrate that includes a piezoelectric material, and the SAW sensor includes a receptor, that binds to a specific target material. Thus, when a solution containing the target material flows across the SAW sensor, its characteristic wavelength is changed by physical, chemical, and/or electrical interactions between the target material and the receptor. The resulting change in a signal (e.g., the characteristic wavelength) can be used to diagnose and monitor the content of the target material.

The SAW sensor is particularly sensitive to the pressure of a liquid, as well as to the viscosity or density of a medium, and corresponding mass changes on the surface of the SAW sensor. Accordingly, precise control of the liquid is desired to minimize noise, which is a signal change due to factors other than the desirably detected mass changes, for example.

SUMMARY

Exemplary embodiments provide a surface acoustic wave ("SAW") device having a pair of interdigitated transducer ("IDT") electrodes, which are resistant to the atmosphere or moisture and are capable of substantially reducing or effectively preventing corrosion caused by contact with chloride ions and reduction in oscillation performance.

According to an exemplary embodiment, a SAW device includes a piezoelectric substrate; and an IDT electrode disposed on the substrate, an oxide film disposed on a surface of the IDT electrode, and a hydrophobic film disposed on a surface of the oxide film.

The IDT electrode may include aluminum, an aluminum alloy, or a combination thereof, and the oxide film may include aluminum oxide.

The oxide film may include artificially or natively formed aluminum oxide.

The hydrophobic film may be disposed by chemically binding a hydrophobic surface modifying agent to the oxide film. The hydrophobic surface modifying agent may include a first functional group, which is hydrophobic, at a first end of the hydrophobic surface modifying agent and a second functional group, which is reactive with the oxide film, at a second end of the hydrophobic surface modifying agent.

The first functional group may be selected from the group consisting of an alkyl group, an alkene group, a fluoro-alkyl group, a fluoro-alkoxy group, a fluoro-alkene group, and a combination thereof. The second functional group may be selected from the group consisting of a carboxyl group, a sulfonic acid group, a phosphonic acid group, and a combination thereof.

In an embodiment, the hydrophobic surface modifying agent may be selected from the group consisting of the following (i) to (v): (i) a fatty acid selected from the group consisting of decenoic acid, stearic acid (octadecanoic acid), capric acid, lauric acid, myristic acid, palmitic acid, dodecenoic acid, tetradecenoic acid, hexadecenoic acid, oleic acid, linoleic acid, linolenic acid, ricinoleic acid, and a derivative thereof, and a combination thereof; (ii) a phosphonic acid compound selected from the group consisting of octyl phosphonic acid, octadecyl phosphonic acid, lauryl phosphonic acid, organophosphonic acid, and a derivative or a salts thereof, and a combination thereof; (iii) a sulfonic acid compound selected from vinylbenzene sulfonic acid, allylsulfonic acid, methallylsulfonic acid, styrenesulfonic acid, isoprenesulfonic acid, 2-acrylamido-2-methylpropanesulfonic acid, organosulfonic acid, or a derivative or a salts thereof, or a combination thereof; a fluorinated compound selected from the group consisting of a fluorinated carboxylic acid, a fluorinated sulfonic acid, a fluorinated organosulfonic acid, a fluorinated phosphonic acid, a perfluorodecanoic acid, a fluorinated organophosphonic acid, or a derivative or a salt thereof, and a combination thereof; and (v) a mixture or a composite of any one or more of the compounds of (i) to (iv).

In an embodiment, the hydrophobic surface modifying agent may be selected from the group consisting of 9-decenoic acid, stearic acid (octadecanoic acid), perfluorooctanoic acid, perfluorodecanoic acid, perfluorobutanesulfonic acid, perfluorooctanesulfonic acid, octadecyl phosphonic acid, and a combination thereof.

A sum of a thickness of the oxide film and a thickness of the hydrophobic film may range from about 1 to about 500 nanometers.

According to another exemplary embodiment, a SAW biosensor includes a piezoelectric substrate; a pair of IDT electrodes disposed on the substrate; a reactive film disposed on the piezoelectric substrate, the reactive film covering the IDT electrodes and combining with a receptor, which can bind to a target material; an oxide film disposed on the surface of the IDT electrodes; and a hydrophobic film disposed on the surface of the oxide film.

The IDT electrode may include aluminum, an aluminum alloy, or a combination thereof, and the oxide film may include aluminum oxide.

The hydrophobic film may be formed by chemically binding a hydrophobic surface modifying agent with the oxide film, wherein the hydrophobic surface modifying agent includes a hydrophobic first functional group at a first end thereof, and a second functional group reactive with the oxide film, at a second end thereof.

The hydrophobic surface modifying agent may be selected from the group consisting of 9-decenoic acid, stearic acid, octadecanoic acid, perfluorooctanoic acid, perfluorodecanoic acid, perfluorobutanesulfonate, perfluorooctanesulfonate, octadecyl phosphonic acid, and a combination thereof.

BRIEF DESCRIPTION OF THE DRAWINGS

The above and other aspects, features and advantages of this disclosure will become more apparent by describing in further detail exemplary embodiments thereof with reference to the accompanying drawings, in which.

DETAILED DESCRIPTION

Figure 1:
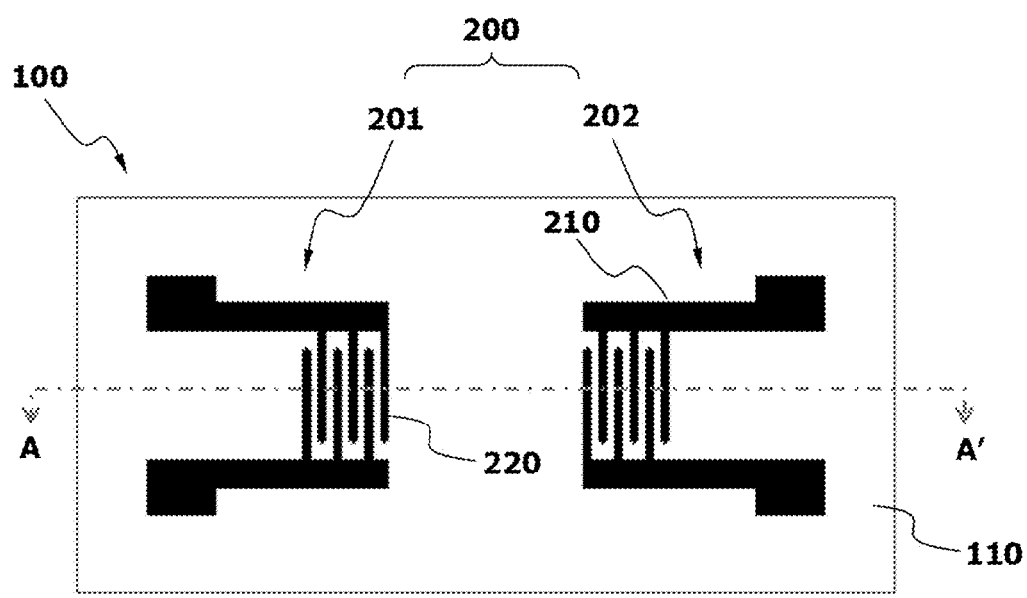
FIG. 1 is a plan view of an exemplary embodiment of a surface acoustic wave ("SAW") device.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer, or section from another element, component, region, layer or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs.

Exemplary embodiments are described herein with reference to cross sectional illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims Hereinafter, exemplary embodiments of the present invention will be described in further detail with reference to the accompanying drawings.

Surface Acoustic Wave ("SAW") Device

Figure 2:
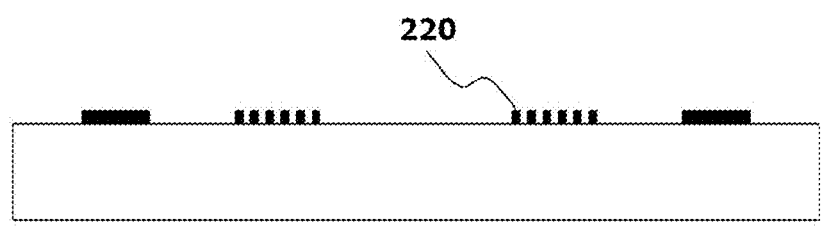
FIG. 2 is a cross-sectional view taken along line A-A' of FIG. 1.
Figure 3:
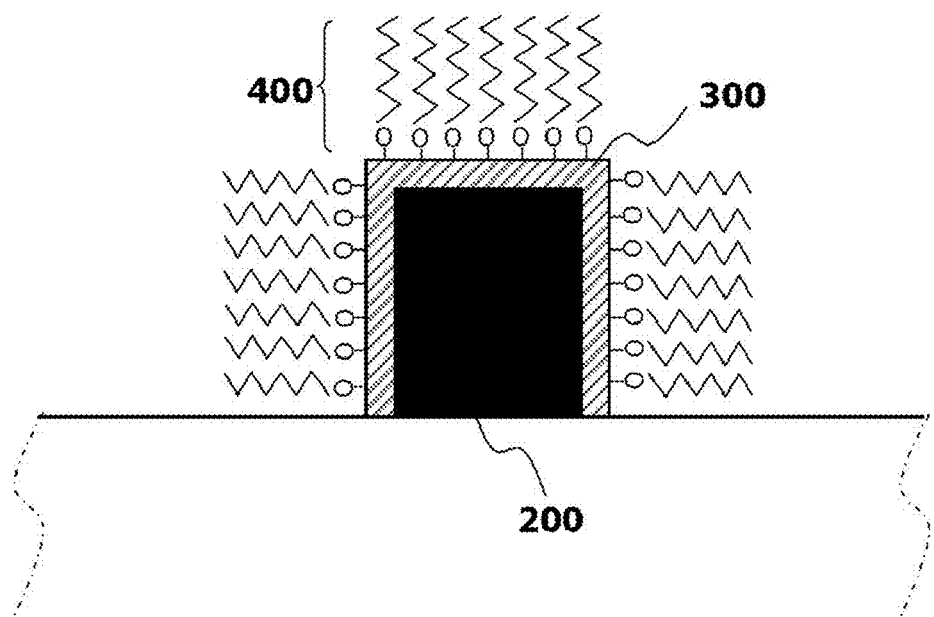
FIG. 3 is a partial cross-sectional view of an interdigitated transducer ("IDT") electrode of the SAW device of FIG. 1.

FIGS. 1 and 2 are plan and cross-sectional views of an exemplary embodiment of a SAW device, and FIG. 3 is a partial cross-sectional view of an interdigitated transducer ("IDT") electrode of the SAW device of FIG. 1. Hereinafter, a SAW device according to the exemplary embodiment will be described with reference to the drawings.

The SAW device 100 according to an exemplary embodiment includes a piezoelectric substrate 110 and at least one IDT electrode 200 formed (e.g., disposed) on the substrate 110. As shown in FIG. 3, an oxide thin film 300 is formed (e.g., disposed) on a surface of the IDT electrode 200, and a hydrophobic thin film 400 is formed (e.g., disposed) on the surface of the oxide thin film 300. The IDT electrode may comprise a metal. Accordingly, when the hydrophobic thin film 400 is disposed on the oxide thin film 300, it is possible to substantially reduce or effectively prevent corrosion of the metal of the IDT electrode.

The substrate 110 comprises a piezoelectric material in which an electrical characteristic (e.g., electric field) is changed when a mechanical signal is applied (i.e., the piezoelectric effect) or in which a mechanical signal is generated when an electrical signal is applied (i.e., the inverse piezoelectric effect). The substrate may comprise, for example, $LiNbO_3$, $LiTaO_3$, $Li_2B_4O_7$, $BaTiO_3$, $PbZrO_3$, $PbTiO_3$, PZT, ZnO, GaAs, quartz, niobate, and a combination thereof.

The IDT electrode 200 is an interface between an electric circuit and an acoustic delay line. The IDT electrode 200 may comprise, or in an embodiment be composed of, a pair of IDTs, specifically a first IDT 201 and a second IDT 202. The first IDT 201 generates a surface acoustic wave by an applied signal. Therefore, the first IDT 201 may be referred to as an "input IDT" or a "transmitter." The surface acoustic wave generated may be transmitted along a surface of the substrate to the second IDT 202 at a selected frequency through expansion and compression and then converted into an electric signal by the inverse piezoelectric effect. The second IDT may be referred to as an "output IDT 202" or a "receiver."

The electrodes of the IDTs are interdigitated, thus the IDT electrodes 200 form a comb shape, and include a bar-shaped electrode 210 and a plurality of finger electrodes 220, which extend from the bar-shaped electrode 210, and a protrusion 230, which extends from the bar-shaped electrode 210. To accommodate the recent trend toward high frequency and miniaturization of electrodes, a pitch between the finger electrodes 220 is desirably narrower. While not wanting to be bound by theory, it is understood that when electrical resistance is reduced by migration of the electrodes and/or a conductive material comes into contact with the IDT electrode 200, a power failure, which is desirably prevented, may occur among the finger electrodes 220. Furthermore, because the IDT electrode 200 may comprise a thin-film metal, such as an aluminum alloy, a copper alloy, or gold, the IDT electrode 200 may corrode when exposed to the atmosphere or moisture. Accordingly, the oxide thin film 300 is formed (e.g., disposed) on the surface of the IDT electrode 200 and may substantially reduce or effectively prevent corrosion of the IDT electrode.

In an embodiment, the IDT electrode 200 may comprise aluminum or an aluminum alloy, and the oxide thin film 300 may comprise aluminum oxide. The aluminum alloy may include Al as the main component and one or more of Ti, Si, Cr, W, Fe, Ni, Co, Pb, Nb, Ta, Zn, and V. The aluminum oxide thin film may be artificially or natively formed aluminum oxide.

The oxide thin film 300 may be formed (e.g., disposed) across an entirety of the IDT electrode 200 or be formed (e.g., disposed) on a portion of the IDT electrode 200. The oxide thin film 300, for example, may be formed by oxidizing the IDT electrode 200 through anodic oxidation. When the oxide thin film 300 is too thick, the weight of the oxide thin film may cause a dumping effect on the surface acoustic wave. In other words, when a thickness h' of the oxide thin film 300 is greater than a film thickness h of the IDT electrode 200, an insertion loss may increase to such a degree that the SAW device cannot operate. The film thickness standardized (e.g., normalized) by the wavelength λ, of a surface acoustic wave is h/λ, and h/λ may be from about 0.001 to about 0.1, specifically about 0.007 to about 0.012, more specifically about 0.01.

Therefore, by simply increasing the thickness of the oxide thin film 300, it is difficult to prevent insertion loss and at the same time protect the IDT electrode 200, which comprises a metal, from moisture.

Furthermore, when the oxide thin film 300 is formed, exposure of the IDT electrode 200 to ions, such as chloride ions, may lead to corrosion of the IDT electrode 200. The corrosion of the IDT electrode 200 may degrade oscillation performance of the IDT electrode 200.

In an exemplary embodiment, the hydrophobic thin film 400 is formed (e.g., disposed) on the surface of the oxide thin film 300. As contact between the ionic solution and the hydrophobic thin film 400 is substantially or entirely blocked, it is possible to substantially reduce or effectively prevent the IDT electrode 200 from corroding.

In an embodiment, the hydrophobic film 400 may be formed (e.g., disposed) by chemically combining a hydrophobic surface modifying agent with the oxide thin film 300.

The hydrophobic surface modifying agent may be a substance in which a first end has a hydrophobic functional group and a second end has a functional group that is reactive with the oxide thin film 300.

The hydrophobic functional group may be selected from the group consisting of an alkyl group, an alkene group, a fluoro-alkyl group, a fluoro-alkoxy group, a fluoro-alkene group, and a combination thereof. The hydrophobic functional group may comprise a $C_1$-$C_{30}$ carbon chain, a $C_1$-$C_{20}$ carbon chain, or a $C_1$-$C_{12}$ carbon chain. While not wanting to be bound by theory, it is understood that the hybrophobicity of the hydrophobic functional group may substantially reduce or effectively block contact between the solution and the IDT electrode.

The functional group having reactivity with the oxide thin film 300 combines the surface of the oxide thin film 300 with the hydrophobic moiety through reaction with the oxide thin film 300. For example, the functional group may be selected from the group consisting of a carboxyl group (—COOH), a sulfonic acid group (—$SO_3H$), and a phosphonic acid group (—$PO_3H_2$).

An exemplary hydrophobic surface modifying agent is an organic acid. When an organic acid contacts the oxide thin film 300, the organic acid may react or be adsorbed. For example, as shown in Reaction Formula 1 or 2, a phosphorus (P) atom of a phosphonic acid group, or a carbon (C) atom of a carboxylic acid group, may form a covalent bond with the aluminum oxide layer (in Reaction Formulas 1 and 2, 'R' represents an organic group). According to an exemplary embodiment, a hydroxyl group (—OH) on the surface of the aluminum oxide thin film 300 is exposed. Without being limited thereto, however, a site that reacts with the surface modifying agent can be formed through various surface treatments.

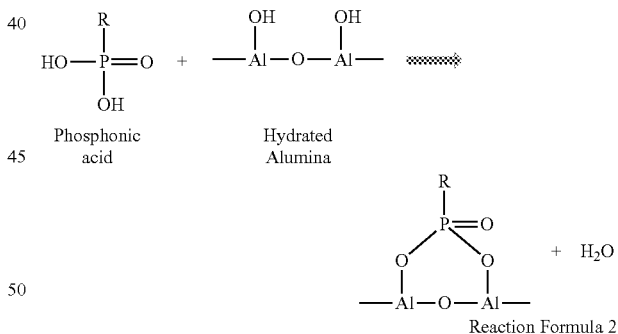

Reaction Formula 1

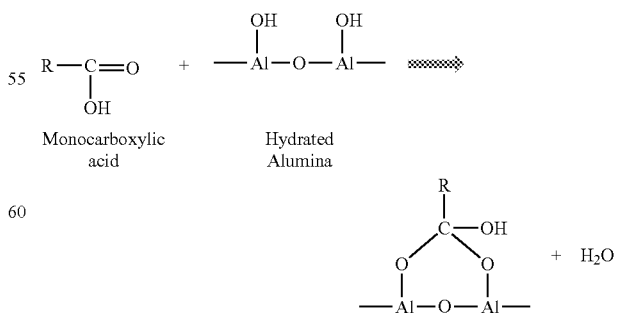

Reaction Formula 2

The hydrophobic surface modifying agent may be a self-assembled monolayer forming material in which one end of the surface modifying agent has a functional group having reactivity with the oxide thin film 300.

When a hydrophobic layer is a self-assembled monolayer and comprises the foregoing hydrophobic surface modifying agent, it is possible to form a uniform hydrophobic surface. The uniform hydrophobic surface improves resistance to moisture or corrosive ions. In addition, it is possible to substantially reduce or effectively prevent oscillation of the IDT electrode from becoming irregular, which can result from a non-uniform layer.

An exemplary hydrophobic surface modifying agent is a saturated or unsaturated $C_8$-$C_{12}$ fatty acid. The hydrophobic surface modifying agent may be selected from the group consisting of decenoic acid, stearic acid (also known as octadecanoic acid), capric acid, lauric acid, myristic acid, palmitic acid, dodecenoic acid, tetradecenoic acid, hexadecenoic acid, oleic acid, linoleic acid, linolenic acid, ricinoleic acid, a derivative thereof, and a combination thereof. Derivatives of the foregoing acids are reactive with the oxide layer, and include the corresponding acid halides, anhydrides, and $C_1$-$C_3$ esters.

The hydrophobic surface modifying agent may be a phosphonic acid compound selected from the group consisting of octylphosphonic acid, octadecylphosphonic acid, lauryl phosphonic acid, organophosphonic acid, and a derivative or a salt thereof, and a combination thereof. Derivatives of the foregoing acids are reactive with the oxide layer, and include the corresponding acid halides, anhydrides, and $C_1$-$C_3$ esters.

In another embodiment, the hydrophobic surface modifying agent may be a sulfonic acid compound selected from the group consisting of vinylbenzene sulfonic acid, allylsulfonic acid, methallylsulfonic acid, styrenesulfonic acid, isoprenesulfonic acid, 2-acrylamido-2-methylpropanesulfonic acid, organosulfonic acid, and a derivative or a salts thereof, and a combination thereof. Derivatives of the foregoing acids are reactive with the oxide layer, and include the corresponding acid chlorides, anhydrides, and $C_1$-$C_3$ esters.

The hydrophobic surface modifying agent may be a fluorinated compound selected from the group consisting of a fluorinated carboxylic acid, a fluorinated sulfonic acid, a fluorinated organosulfonic acid, a fluorinated phosphonic acid, a fluorinated organophosphonic acid, a perfluorodecanoic acid, and a derivative or a salt thereof, and a combination thereof. Derivatives of the foregoing acids are reactive with the oxide layer, and include the corresponding acid chlorides, anhydrides, and $C_1$-$C_3$ esters.

The fluorinated compound may be a perfluorocarboxyl acid, e.g. an acid having the formula $CF_3(CF_2)n$-COOH, in which n is equal to or greater than 7, a perfluorosulfonic acid, e.g., an acid having the formula $CF_3(CF_2)m$-$SO_3H$, in which m is equal to or greater than 1, or the like.

In an embodiment, the hydrophobic surface modifying agent may be selected from the group consisting of 9-decenoic acid, stearic acid (octadecanoic acid), perfluorooctanoic acid, perfluorodecanoic acid, perfluorobutanesulfonic acid, perfluorooctanesulfonic acid, and octadecyl phosphonic acid, and a combination thereof.

A method of forming the hydrophobic thin film 400 on the oxide thin film 300 is not specifically limited, and the method of forming the hydrophobic thin film 400 may include various known chemical surface modification methods.

For example, a substrate, which includes the IDT electrode 200 having the oxide thin film 300 formed thereon, is immersed in solution prepared by dissolving a hydrophobic surface modifying agents in solvent to form the hydrophobic surface 400.

The thicknesses of the oxide thin film 300 and the hydrophobic thin film 400 are not specifically limited. However, when the thickness of these films is excessively large, a frequency characteristic may change due to a weight effect. Also, when the oxide thin film 300 and the hydrophobic thin film 400 are excessively thin, the film formation is not easy to perform, and a desirable effect is not exhibited. The sum of the thicknesses of the oxide thin film 300 and the hydrophobic thin film 400 may range from about 1 to about 500 nanometers (nm), specifically about 5 to about 400 nm, more specifically about 10 to about 100 nm.

The SAW device according to the exemplary embodiment may be a SAW filter or a SAW sensor, for example. In an exemplary SAW device, even when the IDT electrode is exposed to the atmosphere, moisture, a conductive material, an ionic solution, resistance to power is excellent, and power failure and corrosion of the electrodes can be substantially reduced or effectively prevented.

Surface Acoustic Wave ("SAW") Biosensor

Figure 8:
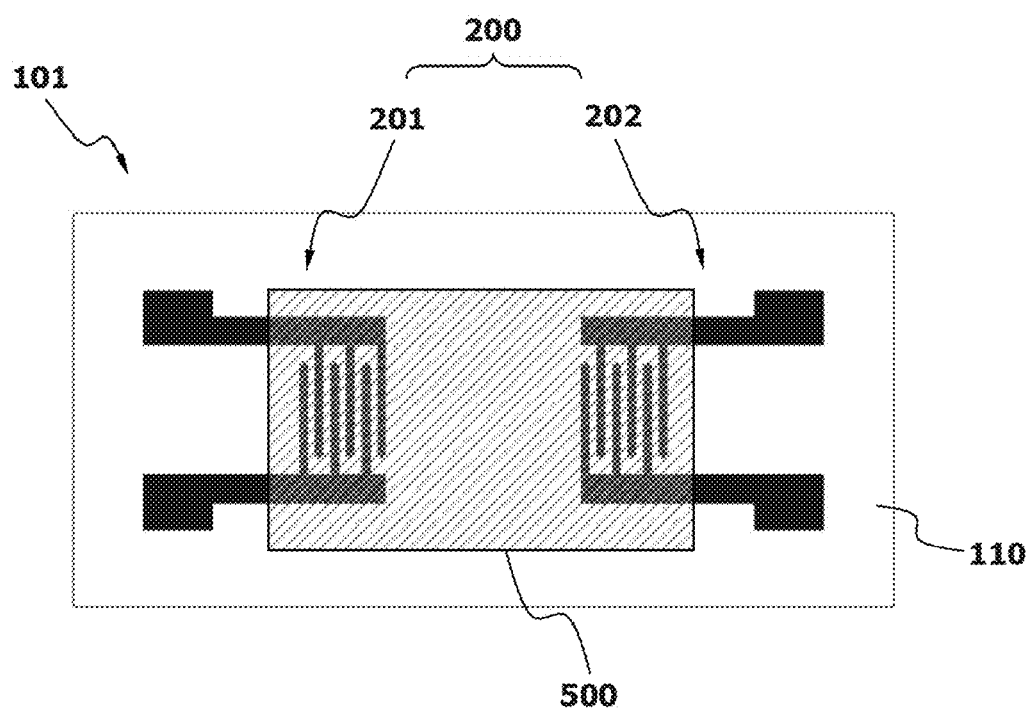
FIG. 8 is a schematic view of an exemplary embodiment of a SAW biosensor.

FIG. 8 is a schematic view of a SAW biosensor according to another exemplary embodiment. Referring to FIG. 8, the SAW biosensor 101 includes a piezoelectric substrate 110; a pair of IDT electrodes including a first IDT electrode 201 and a second IDT electrode 202, which are formed (e.g., disposed) on the substrate 110; and a reactive film 500 which is formed (e.g., disposed) on the piezoelectric substrate 110 to cover the first and second IDT electrodes 201 and 202 and is combined with receptors that can detect a target substance, such as a biological analyte, for example DNA, a protein, an antibody, an antigen, and the like.

Referring to FIGS. 3 and 8, the oxide thin film 300 is formed (e.g., disposed) on the surface of the IDT electrode 200, and the hydrophobic thin film 400 is formed (e.g., disposed) on the surface of the oxide thin film 300, as further described in the description of the SAW device. The materials of the hydrophobic thin film 400 are as described above.

The SAW biosensor 101 can detect a change of a signal resulting from a physical factor, including a change in mass, pressure, density, or viscosity of a medium, to analyze the property of a target material. Furthermore, real-time monitoring can be performed, and the amount of analyte for measurement may be very small.

The operation of the SAW biosensor 101 may be described as follows. An electrical signal generates a mechanical wave while passing through the input IDT electrode 201. A resonance frequency of the wave is changed by physical, chemical, or electrical interactions, as a target material binds to a receptor disposed on the reactive film 500 of the SAW sensor. Thus, in an embodiment, the center frequency, phase, or magnitude of the input signal of the SAW sensor changes. Accordingly, as the change of the signal is observed, it is possible to detect the presence of the target material in the sample. In addition, the target material may be analyzed qualitatively and quantitatively.

In an example, as mass on the SAW sensor surface increases as a target material selectively binds to immobilized receptors on the reactive film 500, a resonance frequency of the surface acoustic wave generated from the input IDT electrode 201 decreases. As the output IDT electrode 202 measures these changes, it is possible to precisely detect the target material and/or a property thereof.

As described above, the IDT electrodes 201 and 202 may comprise aluminum, an aluminum alloy, or a combination thereof. In general, a surface of the aluminum IDT electrodes may corrode, for example when contacted by chloride ions or phosphate ions in a biological solution, such as a chemical fluids or a body fluid, resulting in loss of oscillation. Without protection of the electrodes from corrosion, it would be difficult to use the SAW biosensor to detect a biological molecule.

According to an exemplary embodiment, since the oxide thin film 300 and the hydrophobic thin film 400 are formed (e.g., disposed) on the surface of the IDT electrodes 201 and 202, it is possible to substantially reduce or effectively prevent an attack (e.g., corrosion) by ions existing in biological solution.

In an embodiment, it is possible to diagnose whether a patient has a disease or not by using the SAW biosensor 101 which comprises the reactive film 500 coated with receptors having specific reactivity to the disease analyte.

EXAMPLE 1

Figure 4:
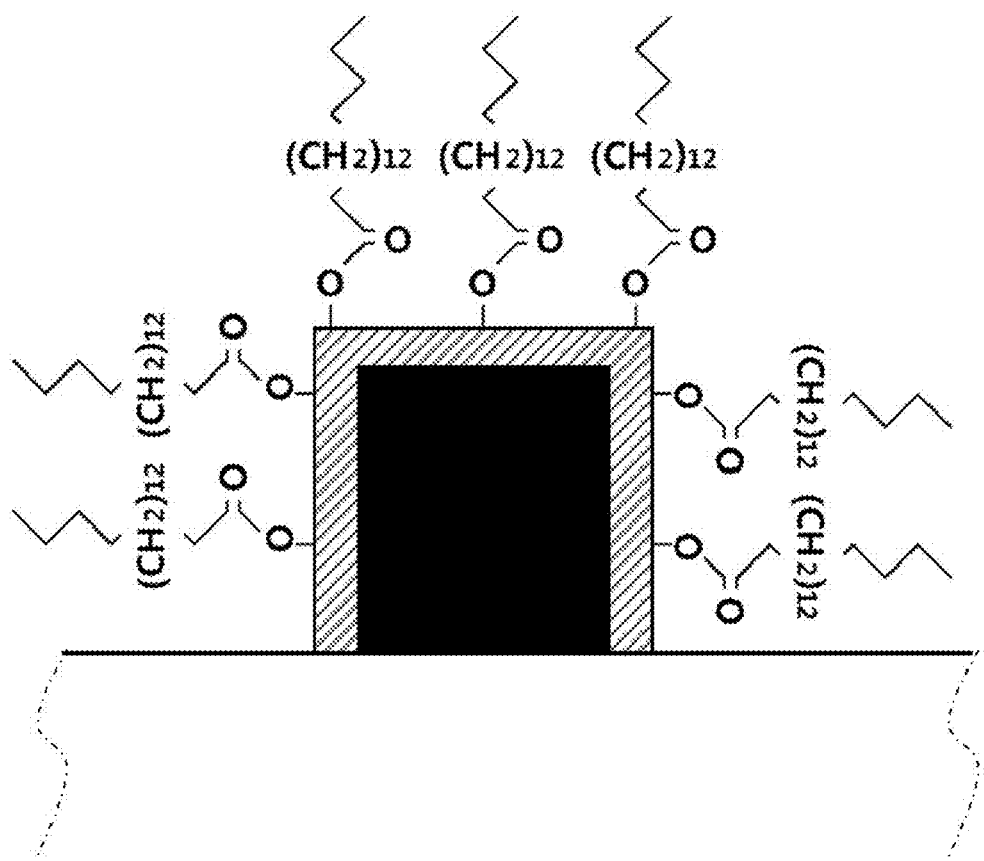
FIG. 4 is a schematic view of an exemplary embodiment of an IDT electrode according to Example 1.

An aluminum oxide thin film is formed on a surface of an aluminum IDT electrode. Then, stearic acid (octadecanoic acid) is combined with the oxide surface to form a hydrophobic thin film. FIG. 4 illustrates an example in which a hydrophobic thin film composed of stearic acid (octadecanoic acid) is formed.

EXAMPLE 2

Figure 5:
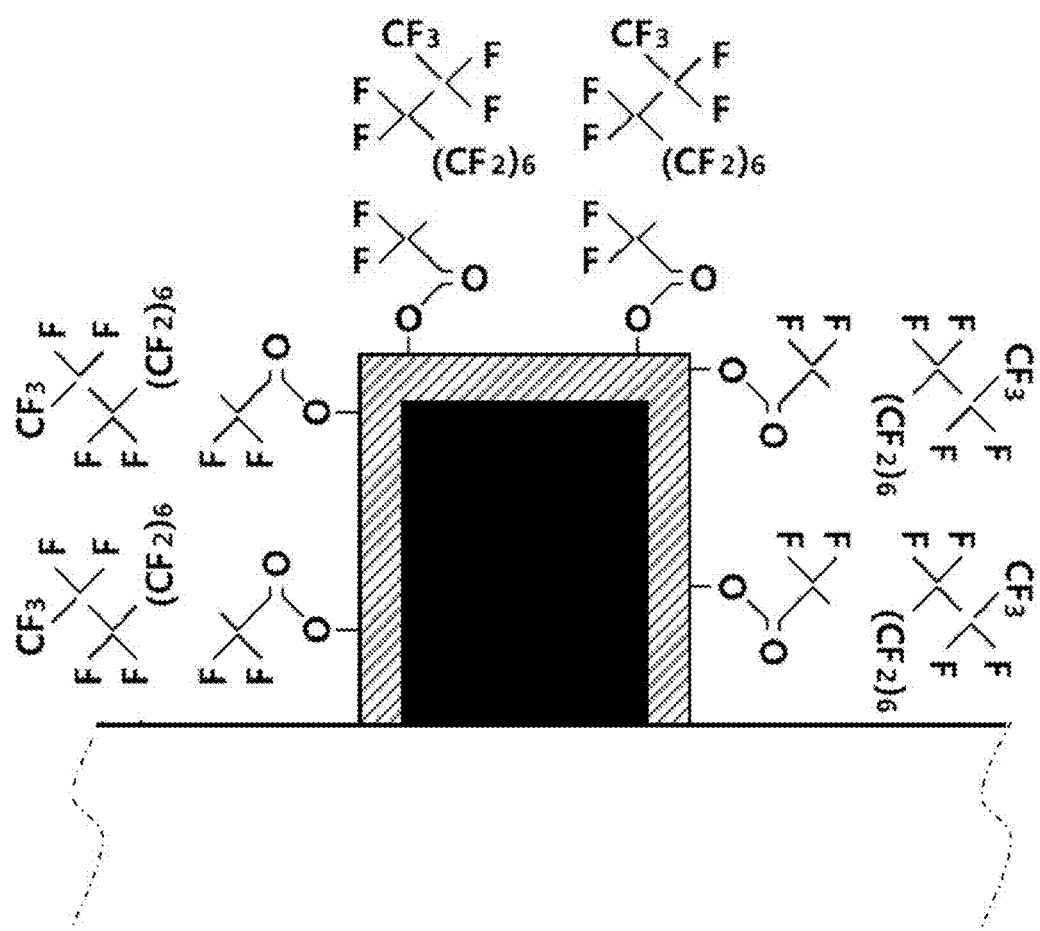
FIG. 5 is a schematic view of an exemplary embodiment of an IDT electrode according to Example 2.

An IDT electrode is manufactured in the same manner as in Example 1, except that perfluorodecanoic acid, a carboxylic acid, to which a fluoro-alkyl chain is connected, is combined with a surface of an oxide thin film to form a hydrophobic thin film, as shown in FIG. 5.

EXAMPLE 3

Figure 6:
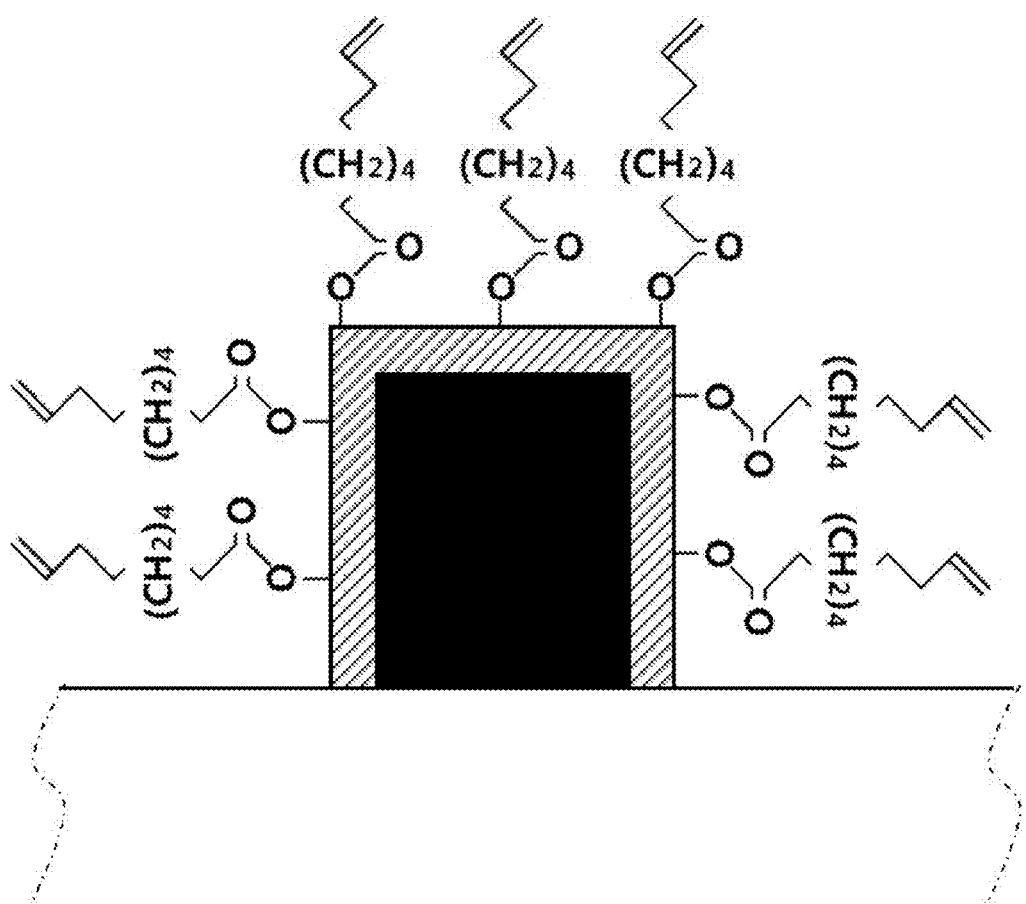
FIG. 6 is a schematic view of an exemplary embodiment of an IDT electrode according to Example 3.

An IDT electrode is manufactured in the same manner as in Example 1, except that 9-decenoic acid, a carboxylic acid, to which an alkyl chain including a terminal alkene group is connected, is combined with a surface of an oxide thin film to form a hydrophobic thin film, as shown in FIG. 6.

EXAMPLE 4

Figure 7:
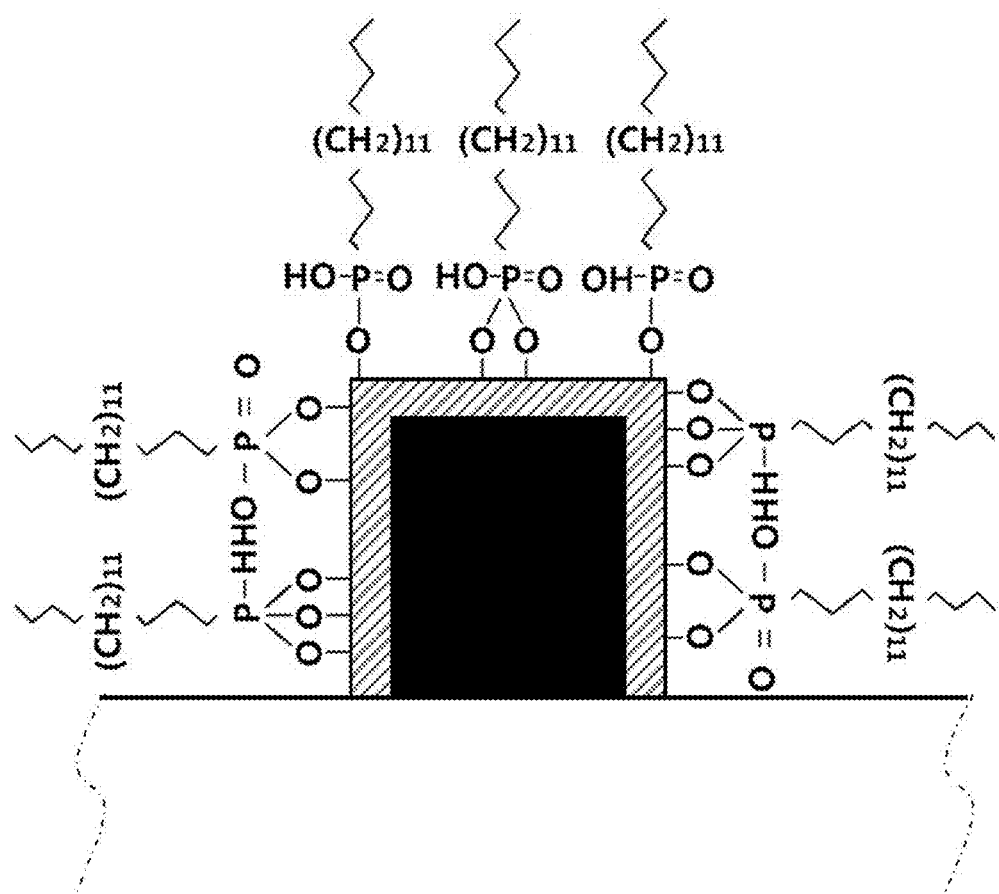
FIG. 7 is a schematic view of an exemplary embodiment of an IDT electrode according to Example 4.

An IDT electrode is manufactured in the same manner as in Example 1, except that octadecyl phosphonic acid, a phosphonic acid, to which an alkyl chain is connected, is combined with a surface of an oxide thin film to form a hydrophobic thin film, as shown in FIG. 7.

EXPERIMENTAL EXAMPLE 1

Figure 9:
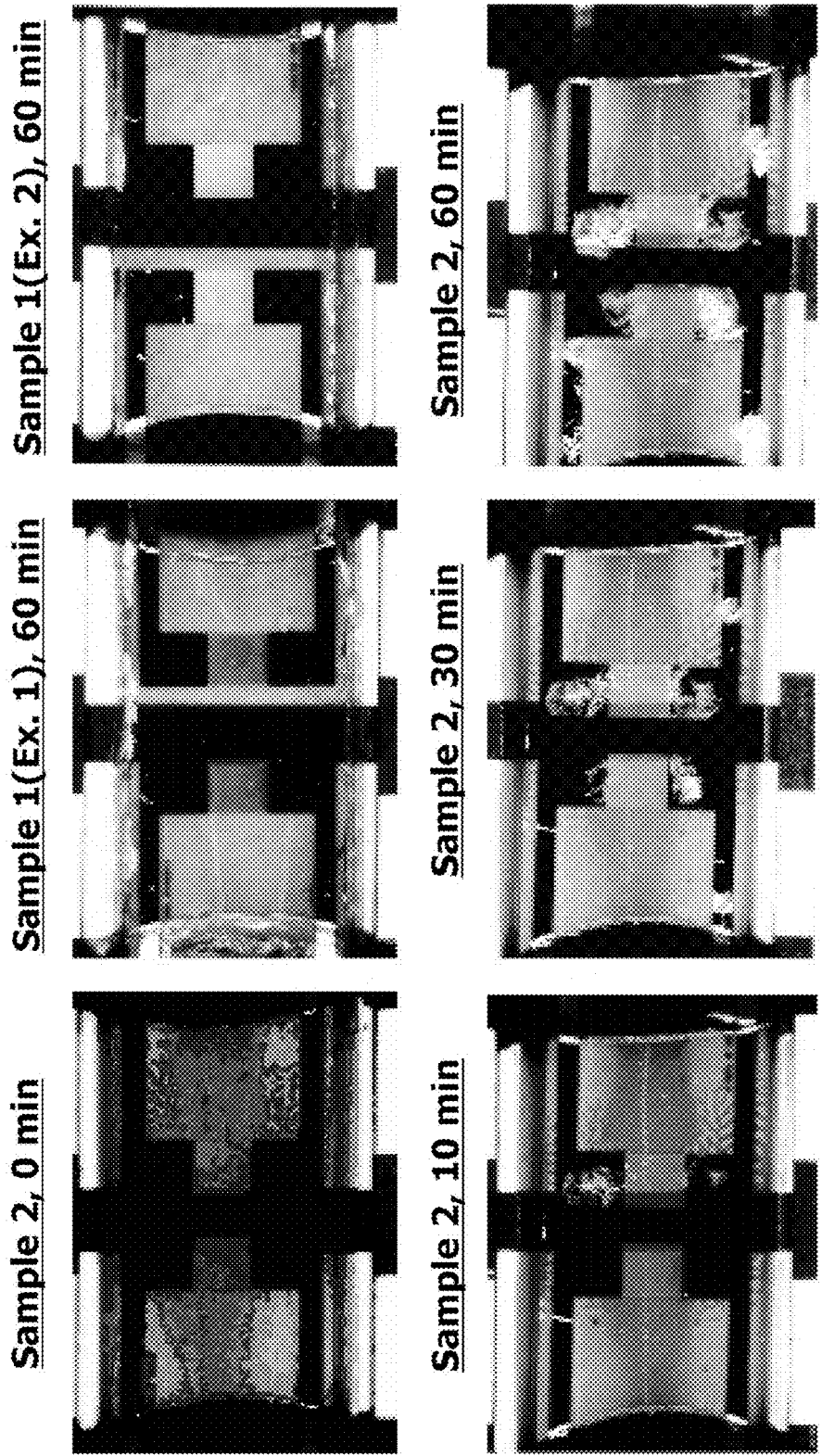
FIG. 9 is a photograph showing the result of Experimental Example 1.

Sample 1, in which an oxide thin film and a hydrophobic thin film are formed on a surface of an aluminum IDT electrode according to Examples 1 and 2, and Sample 2, in which a hydrophobic thin film is not formed on the surface of the electrodes, were exposed to a phosphate-buffered saline ("PBS") solution containing chloride and phosphate ions, and changes were then observed, as shown in FIG. 9.

Referring to FIG. 9, it can be observed that while corrosion occurred within ten minutes in the case of Sample 2, corrosion did not occur in sample 1, even after 60 minutes.

While exemplary embodiments have been disclosed herein, it should be understood that other variations may be possible. Such variations are not to be regarded as a departure from the spirit and scope of exemplary embodiments of the present application, and all such modifications are intended to be included within the scope of the following claims.

What is claimed is:

1. A surface acoustic wave device, comprising:
   a piezoelectric substrate;
   an interdigitated transducer electrode disposed on the substrate;
   an oxide film disposed on a surface of the interdigitated transducer electrode; and
   a hydrophobic thin film disposed on a surface of the oxide film, wherein the hydrophobic thin film comprises a functional group which is bonded to the oxide film, wherein the functional group is selected from the group consisting of a carboxyl group, a sulfonic acid group, a phosphonic acid group, and a combination thereof.

2. The surface acoustic wave device according to claim 1, wherein the interdigitated transducer electrode comprises aluminum, an aluminum alloy, or a combination thereof, and the oxide film comprises an aluminum oxide film.

3. The surface acoustic wave device according to claim 2, wherein the oxide film comprises artificially or natively formed aluminum oxide.

4. The surface acoustic wave device according to claim 1, wherein the hydrophobic film is disposed by chemically binding a hydrophobic surface modifying agents to the oxide film.

5. The surface acoustic wave device according to claim 4, wherein the hydrophobic surface modifying agent comprises a hydrophobic first functional group at a first end of the hydrophobic surface modifying agent, and a second functional group reactive with the oxide film at a second end of the hydrophobic surface modifying agent.

6. The surface acoustic wave device according to claim 5, wherein the hydrophobic first functional group is selected from the group consisting of an alkyl group, an alkene group, a fluoro-alkyl group, a fluoro-alkoxy group, a fluoro-alkene group, and a combination thereof.

7. The surface acoustic wave device according to claim 5, wherein the second functional group reactive with the oxide thin film is selected from the group consisting of a carboxyl group, a sulfonic acid group, a phosphonic acid group, and a combination thereof.

8. The surface acoustic wave device according to claim 5, wherein the hydrophobic surface modifying agent is selected from the group consisting of the following (i) to (v):
   (i) a fatty acid selected from the group consisting of decenoic acid, stearic acid (octadecanoic acid), capric acid, lauric acid, myristic acid, palmitic acid, dodecenoic acid, tetradecenoic acid, hexadecenoic acid, oleic acid, linoleic acid, linolenic acid, ricinoleic acid, and a derivative thereof, and a combination thereof;
   (ii) a phosphonic acid compound selected from the group consisting of octyiphosphonic acid, octadecylphosphonic acid, lauryl phosphonic acid, organophosphonic acid, and a derivative or a salt thereof, and a combination thereof;
   (iii) a sulfonic acid compound selected from the group consisting of vinylbenzene sulfonic acid, allylsulfonic acid, methallylsulfonic acid, styrenesulfonic acid, isoprenesulfonic acid, 2-acrylamido-2-methylpropanesulfonic acid, organosulfonic acid, and a derivative or a salt thereof, and a combination thereof;
   (iv) a fluorinated compound selected from the group consisting of a fluorinated carboxylic acid, a fluorinated sulfonic acid, a fluorinated organosulfuric acid, a fluorinated phosphoric, acid, a perfluorodecanoic acid, a fluorinated organophosphonic acid or a derivative or a salt thereof or a combination thereof; and
   a mixture or a composite of any one or more of compounds (i) to (iv).

9. The surface acoustic wave device according to claim 8, wherein the hydrophobic surface modifying agent is selected from the group consisting of 9-decenoic acid, stearic acid (octadecanoic acid), perfluorodecanoic acid, octadecylphosphonic acid, and a combination thereof.

10. The surface acoustic wave device according to claim 1, wherein a sum of a thickness of the oxide film and a thickness of the hydrophobic film ranges from about 1 to about 500 nanometers.

11. A surface acoustic wave biosensor, comprising:
a piezoelectric substrate;
a pair of interdigitated transducer electrodes disposed on the substrate;
a reactive film disposed on the piezoelectric substrate, the reactive film covering the interdigitated transducer electrodes and combining with a receptor, which can bind to a target material;
an oxide film disposed on a surface of the interdigitated transducer electrodes; and
a hydrophobic film disposed on a surface of the oxide film, wherein the hydrophobic thin film comprises a functional group which is bonded to the oxide film, wherein the functional group is selected from the group consisting of a carboxyl group, a sulfonic acid group, a phosphonic acid group, and a combination thereof.

12. The surface acoustic wave biosensor according to claim 11, wherein the interdigitated transducer electrodes comprise aluminum, an aluminum alloy, or a combination thereof, and the oxide film comprises an aluminum oxide.

13. The surface acoustic wave biosensor according to claim 11, wherein the hydrophobic film is formed by chemically binding a hydrophobic surface modifying agent with the oxide film, wherein the hydrophobic surface modifying agent comprises a first functional group, which is hydrophobic, at a first end thereof, and a second functional group, which is reactive with the oxide film, at a second end thereof.

14. The surface acoustic wave biosensor according to claim 13, wherein the hydrophobic surface modifying agent is selected from the group consisting of the following (i) to (v):
(i) a fatty acid selected from the group consisting of decenoic acid, stearic acid (octadecanoic acid), capric acid, lauric acid, myristic acid, palmitic acid, dodecenoic acid, tetradecenoic acid, hexadecenoic acid, oleic acid, linolenic acid, linolenic acid, ricinoleic acid, and a derivative thereof, and a combination thereof;
(ii) a phosphonic acid compound selected from the group consisting of octylphosphonic acid, octadecylphosphonic acid, iauiyl phosphonic acid, organophosphonic acid, and a derivative or a salt thereof, and a combination thereof;
(iii) a sulfonic acid compound selected from the group consisting of vinylbenzene sulfonic acid, allylsulfonic acid, methallylsulfonic acid, styrenesuifonic acid, isoprenesuifonic acid, 2-acrylamido-2-methylpropanesulfonic acid, organosulfonic acid, and a derivative or a salt thereof, and a combination thereof;
(iv) a fluorinated compound selected from the group consisting of a fluorinated carboxylic acid, a fluorinated sulfonic acid, a fluorinated organosulfuric acid, a fluorinated phosphonic acid, a fluorinated organophosphonic acid, a perfluorodecanoic acid, and a derivative or a salt thereof, and a combination thereof: and
(v) a mixtures or composite of any one or more of the compounds of (i) to (iv).

* * * * *